United States Patent [19]

Aledo

[11] Patent Number: 4,775,375

[45] Date of Patent: Oct. 4, 1988

[54] DISPOSABLE DIAPER WITH ANATOMICAL CONFIGURATION

[76] Inventor: Eduardo C. A. Aledo, AV. Pio XII, 163-Apt No. 12, Campinas, Sao Paulo, Brazil

[21] Appl. No.: 940,717

[22] Filed: Dec. 11, 1986

[30] Foreign Application Priority Data

Dec. 12, 1985 [BR] Brazil .................................. 8506247

[51] Int. Cl.$^4$ ............................................ A61F 13/16
[52] U.S. Cl. ................................. 604/378; 604/385 A
[58] Field of Search .................. 604/385.1, 385.2, 378, 604/379, 380, 374, 375

[56] References Cited

U.S. PATENT DOCUMENTS

| 4,323,070 | 4/1982 | Ternstrom et al. | 604/385.2 |
| 4,324,247 | 4/1987 | Aziz | 604/378 |
| 4,527,990 | 7/1985 | Sigl | 604/385.2 |

Primary Examiner—John D. Yasko
Attorney, Agent, or Firm—Lawrence D. Schuler

[57] ABSTRACT

Disposable diapers with an anatomical configuration and adaptable to the user's body are described herein.

Some of the most usual prior art problems are cutting the material in the crotch portion, shifting of the absorbent structure, discomfort when using a disposable product and less absorbent capacity.

Such problems are solved in the present invention by providing a diaper which has, in combination, a substantially rectangular panel without cuts, an absorbent structure (4), comprising three layers, the first layer (5) allowing liquid penetration, the second layer (6) uniformly distributing the liquid and the third layer retaining the liquid, elastic means (9) in the crotch portion, shrinkable means around the thighs region, and pouch-like formations (12) for retaining said liquid consisting of channels (10) and bulges (11).

2 Claims, 3 Drawing Sheets

DISPOSABLE DIAPER WITH ANATOMICAL CONFIGURATION

The present invention refers to disposable diapers and more specifically to disposable diapers with an elastic structure and an anatomical configuration.

BACKGROUND OF THE INVENTION

Prior art typical disposable diapers are generally composed of basic elements, such as an impermeable backing sheet, an absorbent nucleus and a covering, all of them fixed by an adhesive. Closure elastic members are provided in the region around the thighs, the anatomical form of which is achieved by cutting the diaper material around this region. Adhesive tape strips, projections, edges or the like are used on the diaper sides, in the function of diaper fixing elements placed around the baby's waist.

Several improvements have been introduced in an attempt to solve existing problems, for example, the ones recited in the U.S. Pat. Nos. 4,430,086 and 4,413,623, wherein diapers having elastic bands around the thighs and fixative strips are described.

SUMMARY OF THE INVENTION

One of the objectives of the present invention for solving prior art problems is to provide a substantially rectangular-shaped diaper wherein the anatomical configuration for the user's body is achieved by providing a thermo-shrinkable material on the diaper sides, in combination with transverse elastic bands fixed to the plastic sheet in the crotch region, said bands further providing a greater concentration of absorbent material in said region, thus rendering more absorption.

Another objective of this invention is the use of an absorbent structure having three layers comprising a first layer allowing liquid penetration, a second layer uniformly distributing said liquid over a third layer which retains said liquid.

Therefore, prior art problems are solved by the provision of a diaper wherein its panel is substantially rectangular with not cuts, the absorbent structure thereof having an exceptionally reduced volume and being composed of three layers comprising a first thick layer, the largest of them, the allows liquid penetration, a second thin layer uniformly distributing said liquid and a third thick layer, which has the same area as the second one, for retaining the liquid. The anatomical configuration of the crotch region and of the shrinkable means around the thighs is sensibly improved by combining said elements and means with the above-mentioned absorbent structure, which has reduced volume and high absorption capacity and is corrugated as described henceforth.

BRIEF DESCRIPTION OF THE DRAWINGS

The present invention will be disclosed, based on the drawings wherein.

DETAILED DESCRIPTION OF THE DRAWINGS

Figure 1:
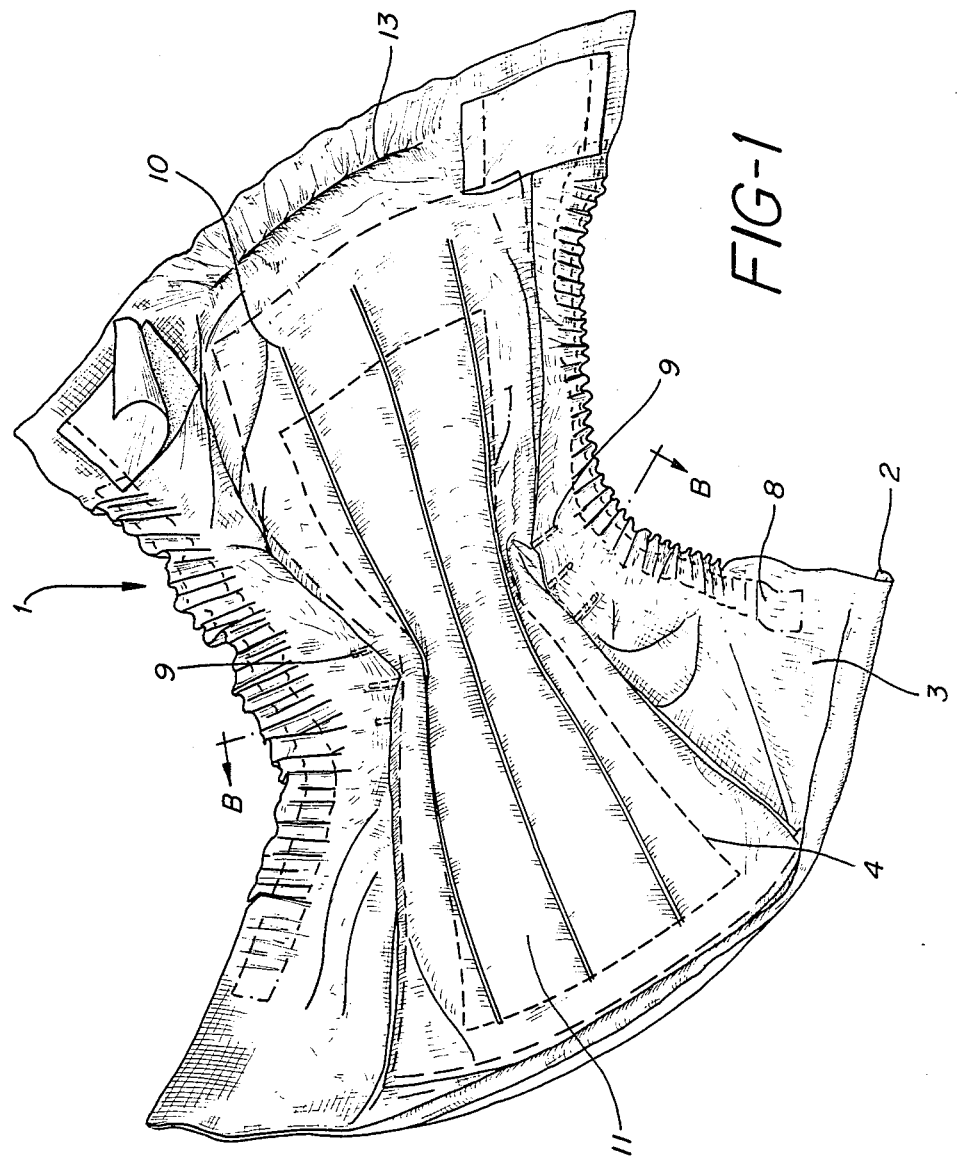
FIG. 1 is a perspective view of the diaper of the present invention, showing the narrowing of the crotch region and its anatomical configuration.

As it can be seen in the drawings, the diaper panel 1, as shown, basically comprises a plastic backing sheet 2, a permeable covering 3 and an absorbent structure 4.

Said permeable covering 3 may comprise a nonwoven fabric made of, for example, polyester fibres, which is aggregated to a plastic polyethylene-based film. After the aggregation stage, the film is perforated in the same pattern of that in the nonwoven fabric.

Due to the high thermo-sealing capacity of the plastic film which is aggregated with the permeable covering, when heat is applied to the covering, it joins to the plastic sheet and to the absorbent structure, eliminating the need of adhesives, thus rendering the set stable, resistant and flexible, since the covering totally links to the absorbent structure and to the sheet preventing said structure from becoming loose, thus providing a better mechanical stability to the product. Loosening is undesirable in that it could cause an undesirable shift of structural components and a consequent inefficiency in absorption.

The absorbent structure 4 is composed of three layers: a first thick layer 5, an intermediate second thin layer 6 and a third thick layer 7, which are all substantially rectangular, layer 5 having an area greater than layers 6 and 7.

The first layer 5 is basically composed of wood pulp (pine, eucalyptus, etc.) or sisal, bamboo pulp or the like, mixed with textile fibre, such as rayon, polyester or polypropylene. The objective of said layer is to provide a better absorption capacity to the structure by causing the liquid to rapidly penetrate into it, thus preventing distribution of the liquid in said layer.

The third layer 7 is composed of wood pulp mixed with synthetic polymers, known as super-absorbents, this composition providing layer 7 with a higher liquid holding capacity.

The intermediate second layer 6, is composed of a paper skin with little absorption capacity but providing a good liquid distribution along layer 7.

The three layers are joined by water-spraying over their interfaces, this originating an interactive layer 6 and forming a single much thinner, absorbent structure, which causes greater comfort to the user and provides, in combination with other inventive elements, a technical effect of improved anatomical configuration and superior adaptability to the user's body. Evaluation results show that when the super-absorbent is present in the third layer, the first layer is left drier, thus providing better comfort to the baby.

Figure 2:
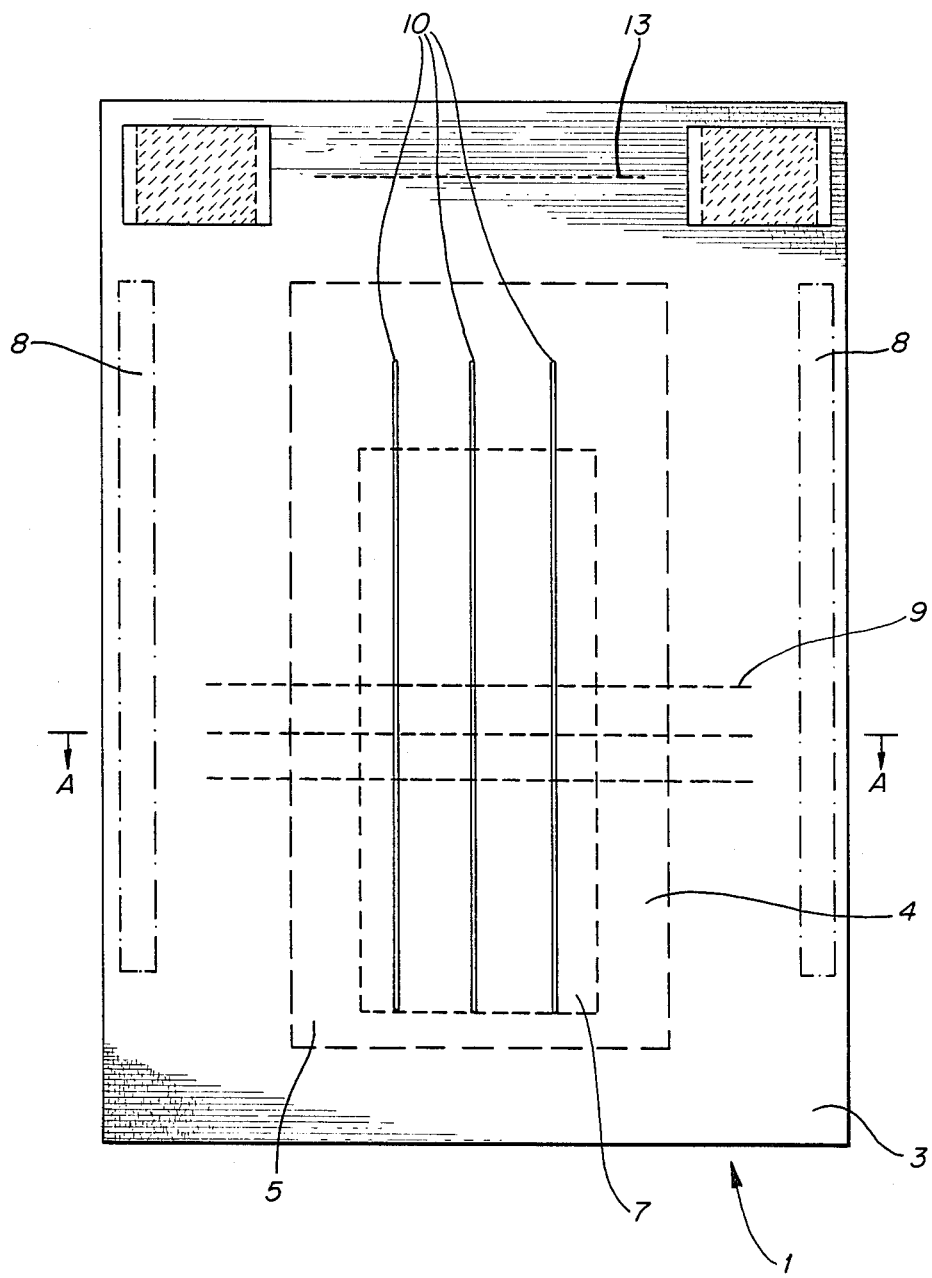
FIG. 2 is an elevational view of the diaper at its non-corrugated position.
Figure 3:
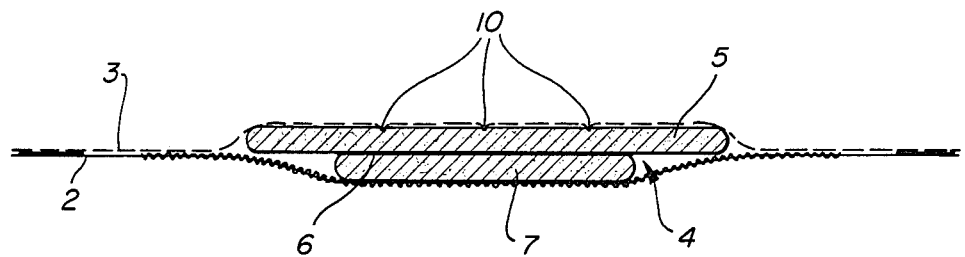
FIG. 3 a sectional view along line A—A on FIG. 2, showing the diaper at its non-corrugated position.
Figure 4:
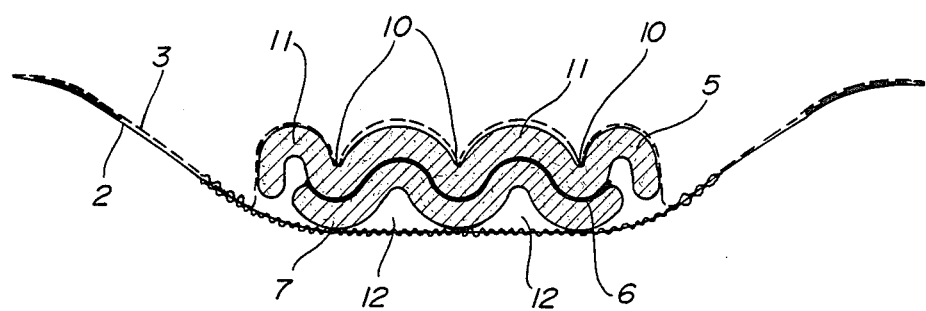
FIG. 4 is a sectional view along line B—B on FIG. 1, showing the diaper at its corrugated position.

As it can be better seen from FIG. 2, the shape of the diaper of the present invention is substantially rectangular, and without cuts. In order to obtain an anatomical shape, adequate to the contour of the baby's thighs, a thermo-shrinkable material having elastomeric characteristics is applied to the sides of the diaper, between covering 4 and sheet 2, and will shrink when heat is applied to it, forming wrinkles which are adaptable to the shape of the legs.

The thermo-shrinkable material comprises a film 8 of a polymer or co-polymer of ethylene vinyl acetate which can also be obtained by mixing plastics, for example, polyethylene or polypropylene, with elastomeric materials or thermoplastic rubber.

This film, when adequately stretched, will have its molecules oriented in a determined direction, longitudinally or transversely, according to the use. The film will shrink when heat is applied to it and when returning to a stable position wrinkles will appear on the sides of the diapers, because film 8 is fixed to covering 3 and sheet 2.

Elastic members are transversely fixed to plastic sheet 2 of diaper 1. Such elastic members 9 are monofilaments made from latex. Said monofilaments are covered with hot-melt adhesive, so both the adhesive holder and the applying roller thereof must be kept hot.

When utilized, the monofilaments are stretched and, on applying adhesive to them, said monofilaments will fix to sheet 2 of the diaper. In order to return to its stable position, said monofilaments will shrink and cause the diaper crotch region to become wrinkled, thus increasing the absorption capacity by the concentration of the absorbent material in this region.

So as to optimize this shrinkage as well as the consequent corrugation of the material, three distribution channels 10 are made by pressing permeable layer 3 along the longitudinal direction of the diaper, so that all the materials interact and lead to the formation of arched portions 11, or bulges which, besides avoiding the formation of undesirable cracks and sulcus, increases the structure stability, thus avoiding permanent deformations due to the corrugated structure resilience.

Another important aspect is a formation of pouches 12 when the monofilament set corrugates. Such punches 12 function as liquid holders if an eventual saturation of the third layer occurs, thus preventing leakage.

An elastic monofilament 13 is also provided in the sheet 2 of the waist portion for better adjusting the diaper around the waist region, thus preventing it from becoming baggy because of excess of material, and making possible the use of any adequate closing means to hold the disposable product on the user. The combination of elastic members 9, thermo-shrinkable materials 8, adsorbent structure 4 with reduced volume and corrugations, and sheets 2 and 3, provides a technical effect of specially anatomical configuration and adaptable to the user's body, eliminating the need for cutting or grooving any diaper element such as the absorbent panel and the sides of the sheet.

Although the preferred embodiment of the present invention has been described and illustrated, the invention is not limited thereto but can be carried out in a different way within the scope of the following claims.

What is claimed is:

1. A disposable diaper of an anatomical configuration having an impermeable backing sheet, a permeable covering and an absorbent structure between said backing sheet and said covering, said permeable covering being fixed to said absorbent structure, characterized by comprising, in combination, a substantially rectangular diaper panel, a three layer absorbent structure comprising a first layer which allows liquid penetration, a second layer which uniformly distributes said liquid and a third layer which retains said liquid, transversely disposed elastic means in the crotch portion, thermo-shrinkable material having elastomeric characteristics in the thigh portions, longitudinally oriented distribution channels, and arched portions between said distribution channels, said first absorbent layer having an area greater than the area of either of said second and third layers and being composed of a mixture of wood pulp with textile fibre, said second layer being thinner than said first layer and said third layer and being composed of a paper skin which results from the wetting of the first and third layers and which fixes said first and second layers to each other, said third layer having the same area as said second layer and being composed of a mixture of wood pulp with synthetic polymers which have super-absorbent characteristics.

2. The disposable diaper of claim 1 wherein said longitudinally oriented distribution channels and said arched portions form reservoir pouches in said diaper, said pouches being located between said third layer and said impermeable backing sheet.

* * * * *